(12) United States Patent
Desai et al.

(10) Patent No.: US 8,501,831 B2
(45) Date of Patent: *Aug. 6, 2013

(54) POLYISOBUTYLENE URETHANE, UREA AND URETHANE/UREA COPOLYMERS AND MEDICAL DEVICES CONTAINING THE SAME

(75) Inventors: Shrojalkumar Desai, Little Canada, MN (US); Marlene C. Schwarz, Auburndale, MA (US); Mark Boden, Harrisville, RI (US); Mohan Krishnan, Shoreview, MN (US); Michael C. Smith, Lino Lakes, MN (US); Frederick H. Strickler, Natick, MA (US); Daniel J. Cooke, Roseville, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/618,148

(22) Filed: Sep. 14, 2012

(65) Prior Publication Data

US 2013/0013040 A1 Jan. 10, 2013

Related U.S. Application Data

(63) Continuation of application No. 12/492,483, filed on Jun. 26, 2009, now Pat. No. 8,324,290.

(60) Provisional application No. 61/076,327, filed on Jun. 27, 2008.

(51) Int. Cl.
*A61N 1/05* (2006.01)
(52) U.S. Cl.
USPC ............ 523/105; 523/112; 528/44; 528/76; 528/85; 528/425
(58) Field of Classification Search
None
See application file for complete search history.

(56) References Cited

U.S. PATENT DOCUMENTS

| | | |
|---|---|---|
| 3,328,372 A | 6/1967 | Thomas et al. |
| 3,427,366 A | 2/1969 | Verdol et al. |
| 3,642,964 A | 2/1972 | Rausch et al. |
| 4,043,331 A | 8/1977 | Martin et al. |
| 4,103,079 A | 7/1978 | Thaler |
| 4,276,394 A | 6/1981 | Kennedy et al. |
| 4,316,973 A | 2/1982 | Kennedy |
| 4,342,849 A | 8/1982 | Kennedy |
| 4,423,185 A | 12/1983 | Matsumoto et al. |
| 4,477,604 A | 10/1984 | Oechsle, III |
| 4,486,572 A | 12/1984 | Kennedy |
| 4,570,270 A | 2/1986 | Oechsle, III |
| 4,675,361 A | 6/1987 | Ward |
| 4,686,137 A | 8/1987 | Ward, Jr. et al. |
| 4,752,626 A | 6/1988 | Hoye et al. |
| 4,767,885 A | 8/1988 | Kennedy |
| 4,771,082 A | 9/1988 | Solodovnik et al. |
| 4,861,830 A | 8/1989 | Ward |
| 4,880,883 A | 11/1989 | Grasel et al. |
| 4,888,389 A | 12/1989 | Kennedy et al. |
| 4,906,673 A | 3/1990 | Mori et al. |
| 4,910,321 A | 3/1990 | Kennedy et al. |
| 4,939,184 A | 7/1990 | Kennedy |
| 5,017,664 A | 5/1991 | Grasel et al. |
| 5,120,813 A | 6/1992 | Ward |
| 5,149,739 A | 9/1992 | Lee |
| 5,194,505 A | 3/1993 | Brugel |
| 5,212,248 A | 5/1993 | Knoll et al. |
| 5,332,791 A | 7/1994 | Knoll et al. |
| 5,340,881 A | 8/1994 | Kennedy et al. |
| 5,428,123 A | 6/1995 | Ward et al. |
| 5,442,010 A | 8/1995 | Hauenstein et al. |
| 5,442,015 A | 8/1995 | Kennedy et al. |
| 5,589,563 A * | 12/1996 | Ward et al. ................. 528/44 |
| 5,637,647 A | 6/1997 | Faust |
| 5,663,234 A | 9/1997 | Kennedy et al. |
| 5,677,386 A | 10/1997 | Faust |
| 5,741,331 A | 4/1998 | Pinchuk |
| 5,852,118 A | 12/1998 | Horrion et al. |
| 5,874,484 A | 2/1999 | Dirckx et al. |
| 6,005,051 A | 12/1999 | Kennedy et al. |

(Continued)

FOREIGN PATENT DOCUMENTS

| | | |
|---|---|---|
| JP | 11131325 A | 5/1999 |
| WO | WO8704625 A1 | 8/1987 |

(Continued)

OTHER PUBLICATIONS

Ako, Masayuke et al., "Polyisobutylene-based urethane foams I. Comparative reactivities of hydroxyl-terminated polyisobutylene-diols and -triols and other hydroxyl-capped polyols with isocyanate", Polymer Bulletin 19(2), 137-143 (1988).

Ako, Masayuke et al., "Polyisobutylene-based urethane foams II. Synthesis and properties of novel polyisobutylene-based flexible polyurethane foams", Journal of Applied Polymer Science, vol. 37(5), Feb. 5, 1989, pp. 1351-1361.

Bela et al., Living Carbocation Polymerization. XX. Synthesis of Allyl-Telechelic Polyisobutylenes by One-Pot Polymerization-Functionalization polymer. Mater. Sci. Eng. 1988; 58:869-872.

(Continued)

*Primary Examiner* — Marc Zimmer
(74) *Attorney, Agent, or Firm* — Faegre Baker Daniels LLP

(57) ABSTRACT

The present invention pertains to polyisobutylene urethane, urea and urethane/urea copolymers, to methods of making such copolymers and to medical devices that contain such polymers. According to certain aspects of the invention, polyisobutylene urethane, urea and urethane/urea copolymers are provided, which comprise a polyisobutylene segment, an additional polymeric segment that is not a polyisobutylene segment, and a segment comprising a residue of a diisocyanate. According to other aspects of the invention, polyisobutylene urethane, urea and urethane/urea copolymers are provided, which comprise a polyisobutylene segment and end groups that comprise alkyl-, alkenyl- or alkynyl-chain-containing end groups.

17 Claims, No Drawings

U.S. PATENT DOCUMENTS

| | | |
|---|---|---|
| 6,010,715 A | 1/2000 | Wick et al. |
| 6,072,003 A | 6/2000 | Horrion et al. |
| 6,093,197 A | 7/2000 | Bakula et al. |
| 6,200,589 B1 | 3/2001 | Kennedy et al. |
| 6,228,945 B1 | 5/2001 | Kennedy et al. |
| 6,365,674 B1 | 4/2002 | Kaufhold et al. |
| 6,444,334 B1 | 9/2002 | Doi et al. |
| 6,545,097 B2 | 4/2003 | Pinchuk et al. |
| 6,555,619 B1 | 4/2003 | Kennedy et al. |
| 6,600,956 B2 | 7/2003 | Maschino et al. |
| 6,627,724 B2 | 9/2003 | Meijs et al. |
| 6,849,667 B2 | 2/2005 | Haseyama et al. |
| 6,870,024 B2 | 3/2005 | Haubennestel et al. |
| 7,101,956 B2 | 9/2006 | Benz et al. |
| 7,105,622 B2 | 9/2006 | Kennedy et al. |
| 7,196,142 B2 | 3/2007 | Kennedy et al. |
| 7,292,890 B2 | 11/2007 | Whitehurst et al. |
| 7,347,751 B2 | 3/2008 | Sweeney et al. |
| 7,553,546 B1 | 6/2009 | Tan |
| 7,715,922 B1 | 5/2010 | Tan |
| 8,324,290 B2 * | 12/2012 | Desai et al. .................. 523/105 |
| 2003/0125499 A1 | 7/2003 | Benz et al. |
| 2003/0204022 A1 | 10/2003 | Kennedy et al. |
| 2004/0054210 A1 | 3/2004 | Benz et al. |
| 2004/0198901 A1 | 10/2004 | Graham et al. |
| 2005/0031874 A1 | 2/2005 | Michal et al. |
| 2005/0060022 A1 | 3/2005 | Felt et al. |
| 2005/0288476 A1 | 12/2005 | Yilgor et al. |
| 2006/0047083 A1 | 3/2006 | Yilgor et al. |
| 2006/0223946 A1 | 10/2006 | Faust et al. |
| 2006/0264577 A1 | 11/2006 | Faust et al. |
| 2007/0051531 A1 | 3/2007 | Borganonkar et al. |
| 2007/0093604 A1 | 4/2007 | Kennedy et al. |
| 2007/0203302 A1 | 8/2007 | Kennedy et al. |
| 2007/0282411 A1 | 12/2007 | Franz et al. |
| 2008/0167423 A1 | 7/2008 | Richards et al. |
| 2009/0187162 A1 | 7/2009 | Ohara et al. |
| 2009/0326077 A1 | 12/2009 | Desai et al. |
| 2010/0023104 A1 | 1/2010 | Desai et al. |
| 2010/0069578 A1 | 3/2010 | Faust et al. |
| 2010/0075018 A1 | 3/2010 | Desai et al. |
| 2010/0107967 A1 | 5/2010 | Tanaka et al. |
| 2010/0179298 A1 | 7/2010 | Faust et al. |
| 2010/0241208 A1 | 9/2010 | Pinchuk |
| 2011/0054580 A1 | 3/2011 | Desai et al. |
| 2011/0054581 A1 | 3/2011 | Desai et al. |
| 2012/0077934 A1 | 3/2012 | Faust et al. |

FOREIGN PATENT DOCUMENTS

| | | |
|---|---|---|
| WO | WO9322360 A1 | 11/1993 |
| WO | WO9526993 A1 | 10/1995 |
| WO | WO9700293 A1 | 1/1997 |
| WO | WO9747664 A1 | 12/1997 |
| WO | WO9833832 A1 | 8/1998 |
| WO | WO03042273 A1 | 5/2003 |
| WO | WO2004014453 A1 | 2/2004 |
| WO | WO2004044012 A1 | 5/2004 |
| WO | WO2004113400 A2 | 12/2004 |
| WO | WO2006011647 A1 | 10/2006 |
| WO | WO2007117566 A2 | 10/2007 |
| WO | WO2008060333 A1 | 5/2008 |
| WO | WO2008066914 A1 | 6/2008 |
| WO | WO2008112190 A1 | 9/2008 |
| WO | WO2008127730 A1 | 10/2008 |
| WO | WO2008156806 A1 | 12/2008 |
| WO | WO2009058397 A1 | 5/2009 |
| WO | WO2009158600 A1 | 12/2009 |
| WO | WO2009158609 A1 | 12/2009 |
| WO | WO2010039986 A1 | 4/2010 |
| WO | WO2010081132 A1 | 7/2010 |
| WO | WO2010111280 A1 | 9/2010 |
| WO | WO2011022583 A1 | 2/2011 |
| WO | WO2011060161 A1 | 5/2011 |

OTHER PUBLICATIONS

Chang, Victor S.C. et al. "Gas Permeability, Water Absorption, Hydrolytic Stability and Air-Oven Aging of Polyisobutylene-Based Polyurethane Networks", Polymer Bulletin 8(2-3-4), 69-74 (1982).

Cozzens, David et al., "Long term in vitro biostability of segmented polyisobutylene-based thermoplastic polyurethanes", Journal of Biomedicals Materials Research Journal, 2010, pp. 1-9.

De, Priyadarsi et al., "Carbocationic Polymerization of Isobutylene Using Methylaluminum Bromide Coinitiators: Synthesis of Bromoally Functional Polyisobutylene" Macromolecules, Oct. 2006, 39(2), 7527-7533.

De, Priyadarsi et al., "Relative Reactivity of C4 Olefins toward the Polyisobutylene Cation" Macromolecules 2006, 39, 6861-6870.

Erdodi, G., et al., "Polyisobutylene-Based Polyurethanes. III. Polyurethanes Containing PIB/PTMO Soft Co-Segments," J. Polym. Sci., Part A: Polym. Chem, 47:5278-5290 (2009).

Erdodi, G., et al., "Polyisobutylene-Based Polyurethanes. VI. Unprecedented Combination of Mechanical Properties and Oxidative/Hydrolytic Stability by H-Bond Acceptor Chain Extenders" J. Polym. Sci., Part A: Polym. Chem, 48:2361-2371 (2010).

Faust, R. et al., "Method to Prepare Block Copolymers by the Combination of Cationic and Anionic Polymerization", U.S. Appl. No. 12/225,905, filed Apr. 5, 2007.

Gadkari A. et al., "Preparation and biocompatibility of Novel Polar-Nonpolar Networks. Osynthesis, Characterization and Histological-Bacterial Analysis of Mixed Polytetrahydrofuran-Polyisobutylene Networks", Polymer Bulletin, vol. 22, No. 1, Jul. 1, 1989, pp. 25-32.

Giusti, Paolo et al., "Synthesis and Characterization of New potentially Hemocompatible Thermoplastic Elastomers", p. 371, Abstract.

Gunatillake, P.A. et al., "Poly(dimethylsiloxane)/Poly(hexamethylene oxide) Mixed Macrodiol Based Polyurethane Elastomers. I. Synthesis and Properties", Journal of Appl. Polym. Sci. 2000, 76, 2026-2040, © 2000.

Higashihara, T. et al., "Synthesis of Poly(isobutylene-block-methyl methacrylate) by a Novel Coupling Approach", Macromolecules, 39:5275-5279 (2006).

International Search Report and Written Opinion issued in PCT/US2006/013308, dated Aug. 25, 2006.

International Search Report and Written Opinion issued in PCT/US2007/008528, dated Oct. 2, 2007.

International Search Report and Written Opinion issued in PCT/US2007/012948, dated Nov. 28, 2007.

International Search Report and Written Opinion issued in PCT/US2010/028334, Dated May 6, 2010, 12 pages.

International Search Report and Written Opinion issued in PCT/US2010/047633, Dated Jun. 17, 2011, 12 pages.

International Search Report and Written Opinion issued in PCT/US2010/047633, Jun. 17, 2011, 12 pages.

International Search Report and Written Opinion issued in PCT/US2010/047703, Dated Jun. 17, 2011, 12 pages.

International Search Report and Written Opinion issued in PCT/US2010/047703, mailed Jun. 17, 2011, 12 pages.

International Search Report issued in PCT/US2009/048827, mailed Oct. 6, 2009, 3 pages.

International Search Report issued in PCT/US2009/048845, mailed Oct. 6, 2009, 3 pages.

International Search Report issued in PCT/US2010/020733, mailed May 6, 2010.

Ioffe, David et al., "Bromine, Organic Compounds", Kirk-Othmer Encyclopedia of Chemical Technology, vol. 4, pp. 340-365, © 2002.

Ivan, B. et al., "Synthesis of New Polyisobutylene-Based Polyurethanes", Am. Chem. Soc., Div. Org. Coat. Plast. Prepr., 43, 908-913 (1980).

Jenny, C. et al., "A New Insulation Material for Cardiac Leads with Potential for Improved performance", HRS 2005, HeartRhythm, 2, S318-S319 (2005).

Jewrajka, Suresh K. et al., "Polyisobutylene-Based Polyurethanes. II. Polyureas Containing Mixed PIB/PTMO Soft Segments", Journal of Polymer Science: Part A: Polymer Chemistry, vol. 47, 2787-2797 (2009).

Jewrajka, Suresh K. et al., "Polyisobutylene-Based Segmented Polyureas. I. Synthesis of Hydrolytically and Oxidatively Stable Polyureas", Journal of Polymer Science: Part A: Polymer Chemistry, vol. 47, 38-48 (2009).

Kang, Jungmee et al, "PIB-Based Polyurethanes. IV. The Morphology of Polyurethanes Containing Soft Co-Segments", Journal of Polymer Science Part A: Polymer Chemistry, vol. 47, 6180-6190 (2009).

Kang, Jungmee et al., "Rendering Polyureas Melt Processable", Journal of Polymer Science Part A: Polymer Chemistry, vol. 49, 2461-2467 (2011).

Kang, Jungmee et al., Polyisobutylene-Based Polyurethanes. V. Oxidative-Hydrolytic Stability and Biocampatibility, Journal of Polymer Science: Part A: Polymer Chemistry, vol. 48, 2194-2203 (2010).

Kennedy, J.P. et al., "Designed Polymers by Carbocationic Macromolecular Engineering: Theory and practice", Hanser Publishers 1991, pp. 191-193 and 226-233.

Kennedy, J.P. et al., "Polyisobutylene-Based Diols and Polyurethanes", Urethane Chemistry and Applications, Ed., K. H. Edwards, ACS Symp. Book Series, 172, Washington, D.C. 1981, pp. 383-391.

Kennedy, J.P. et al., "Polyisobutylene-Based Diols and Polyurethanes" Advances in Urethane Science and Technology, vol. 8, 1981, pp. 245-251.

Kennedy, J.P. et al., "Polyisobutylene-based Model urethane Networks, I. Initial characterization and Physical properties", Polymeric Materials Science and Engineering, vol. 49, Copyright 1983 by ACS, pp. 69-77.

Kennedy, Joseph P. Synthesis, Characterization and Properties of Novel Polyisobutylene-Based urethane Model Networks, Journal of Applied Polymer Science, vol. 33(7), May 20, 1987, pp. 2449-2465.

Kennedy, Joseph P. "Synthesis, Characterization and Properties of Polyisobutylene-Based Polyurethanes", 6th International Technical/Marketing Conference: Polyurethane-New Paths to Progress-Marketing—Technology, Journal of Cellular Plastics, 1983, 19:288-307.

Kennedy, Joseph P. "Synthesis, Characterization and Properties of Polyisobutylene-Based Polyurethanes", Journal of Elastomers and Plastics, vol. 17 (Jan. 1985), pp. 82-88.

Kennedy, Joseph P. "Synthesis, Characterization and Properties of Polyisobutylene-Based Polyurethanes", The Society of the Plastics Industry, Inc., polyurethane Division, Proceedings of the SPI—6th International Technical/Marketing Conference, Nov. 2-4, 1983, San Diego, CA, pp. 514-516.

Kennedy, Joseph P., "Polyurethanes Based on Polyisobutylenes", Chemtech, Nov. 1986, 16(11), pp. 694-697.

Lelah, M.D. et al., "Polyurethanes in Medicine", CRC Press, Boca Raton, FL 1986, Chapter 3.

Li, J. et al., "Polyisobutylene supports—a non-polar hydrocarbon analog of PEG supports", Tetrahedron, 61 (51):12081-12092, Dec. 2005.

Macias, A. et al., "Preparacion y reticulacion de poliisobutilenos de bajo peso molecular con grupos terminales reactivos", Revista de Plasticos Modernos, Num 332 (Apr. '83), pp. 412-418.

Miller, J. A., "New Directions in Polyurethane Research", Organic Coatings and Applied Polymer Science Proceedings, vol. 47, Copyright 1982 by ACS, pp. 124-129.

Mitzner, E. et al., "Modification of poly(ether urethane) elastomers by incorporation of poly(isobutylene) glycol. Relation between polymer properties and thrombogenicity", J. Biomater. Sci. Polymer edn. vol. 7, No. 12, pp. 1105-1118 (1996).

Mitzner, E., "Modification of segmented poly(ether urethanes) by incorporation of Poly(isobutylene)glycol", J.M.S.—Pure Appl. Chem., A34(1), pp. 165-178 (1997).

Miyabayashi, Toshio et al., "Characterization of Polyisobutylene-Based Model Urethane Networks", Journal of Applied Polymer Science, vol. 31, pp. 2523-2532 (1986).

Muller, J.P. et al., "Surface modification of polyurethanes by multicomponent polyaddition reaction", Journal of Materials Science Letters 17(2), 1998, pp. 115-118.

Non-Final Office Action issued in U.S. Appl. No. 11/400,059, mailed Apr. 11, 2011.

Non-Final Office Action issued in U.S. Appl. No. 12/492,483, mailed Nov. 21, 2011, 11 pages.

Non-Final Office Action, issued in U.S. Appl. No. 12/685,858, mailed Feb. 15, 2012, 18 pages.

Notice of Allowance issued in U.S. Appl. No. 12/492,483, mailed Jul. 13, 2012, 9 pages.

Office Action issued in U.S. Appl. No. 11/400,059, mailed Aug. 24, 2010.

Ojha et al., "Synthesis and Characterization of Thermoplastic Polyurethaneureas based on Polyisobutylene and Poly (tetramethylene oxide) Segments", J. Macromolecular Science, Part A, vol. 47(3), pp. 186-191, Mar. 2010.

Ojha, Umaprasana et al., "Syntheses and characterization of novel biostable polyisobutylene based thermoplastic polyurethanes", Polymer 50(2009), 3448-3457.

Ojha, Umaprasana et al., "Synthesis and Characterization of Endfunctionalized Polyisobutylenes for Sharpless-type Click Reactions", Polymer Preprints 2007, 48(2), 786.

Puskas, J.E. et al., "Polyisobutylene-based biomaterials", Journal of Polymer Science Part A: Polymer Chemistry, vol. 42, Issue 13 (2004) pp. 3091-3109.

Rajkhowa, Ritimoni et al., "Efficient syntheses of hydroxyallyl end functional polyisobutylenes, a precursors to thermoplastic polyurethanes", Polymer Reprints (American Chemical Society, Division of Polymer Chemistry) 2007, 48 (2), 233-234.

Ranade, S. et al., "Physical characterization of controlled release of paclitaxel from the TAXUS™ Express2™ drug-eluting stent", Journal of Biomedical Materials Research Part A, 71A (2004) 625-634.

Ranade, S.V. et al., Styrenic Block copolymers for Biomaterial and Drug Delivery Applications, Acta Biomater. Jan. 2005; 1(1): 137-44.

Santos, R. et al., "New Telechelic Polymers and Sequential Copolymers by Polyfunctional Initiator-Transfer-Agents (Inifers)", Polymer Bulletin, 11:341-348 (1984).

Simmons, Anne. et al., "The effect of sterilisation on a poly(dimethylsiloxane)/poly(hexamethylene oxide) mixed macrodiol-based Polyurethane elastomer", Biomaterials 2006, 27, 4484-4497.

Speckhard, T.A. et al., "New generation polyurethanes", Polymer News 1984, 9(12), 354-358.

Speckhard, T.A. et al., "Properties of Polyisobutylene Polyurethane Block Copolymers: 2. Macroglycols produced by the 'inifer' technique", Polymer, vol. 26, No. 1, Jan. 1985, pp. 55-78.

Speckhard, T.A. et al., "Properties of Polyisobutylene Polyurethane Block Copolymers: 3. hard segments based on 4,4'-dicyclohexylmethane diisocyanate (H12MDI) and butane diol", Polymer, vol. 26, No. 1, Jan. 1985, pp. 70-78.

Speckhard, T.A. et al., "Properties of Polyisobutylene-Polyurethane Block Copolymers", Journal of Elastomers and Plastics, vol. 15 (Jul. 1983), pp. 183-192.

Speckhard, T.A. et al., "Properties of Polyisobutylene-Polyurethane Block Copolymers: I. Macroglycols from Ozonolysis of Isobutylene-Isoprene Copolymer", Polymer Engineering and Science, Apr. 1983, vol. 23. No. 6, pp. 337-349.

Speckhard, T.A. et al., "Ultimate Tensite Properties of Segmented Polyurethane Elastomers", Rubber Chem. Technol., 59, 405-431 (1986).

Tan, J. et al., "In Vivo Biostability Study of a New Lead Insulation Material," Cardiostim 2006, Europace Supplements, 8, 179PW/9 (2006).

Tonelli, C. et al., "New Fluoro-Modified Thermoplastic Polyurethanes" Journal of Applied Polymer Science, vol. 87, Issue 14 (2003) 2279-2294.

Virmani, R. et al. Circulation Feb. 17, 2004, 109)6) 701-5.

Wang, F. Polydimethylsiloxane Modification of Segmented Thermoplastic Polyurethanes and Polyureas, PhD. Dissertation, Virginia Polytechnic Institute and State university, Apr. 13, 1998.

Weisberg, David M. et al., "Synthesis and Characterization of Amphiphilic Poly(urethaneurea)-comb-polyisobutylene Copolymers", Macromolecules 2000, 33(12), pp. 4380-4389.

Weissmuller, M. et al., "Preparation and end-linking of hydroxyl-terminated polystyrene star macromolecules", Macromolecular Chemistry and Physics 200(3), 1999, 541-551.

Wiggins, Michael J. et al., "Effect of soft-segment chemistry on polyurethane biostability during in vitro fatigue loading", Journal of biomedical materials research, 68(4), 2004, 668-683.

Wohlfarth, C., "Permittivity (Dielectric Constant) of Liquids", CRC Handbook, 91st ed. 2010-2011, pp. 6-186 to 6-207.

Wright, James I., "Using Polyurethanes in Medical Applications", 5 pages. Downloaded from http://www.cmdm.com on Oct. 17, 2006.

Wu, Yuguang et al., "The role of adsorbed fibrinogen in platelet adhesion to polyurethane surfaces: A comparison of surface hydrophobicity, protein adsorption, monoclonal antibody binding, and platelet adhesion", Journal of Biomedical Materials Research, Part A, Sep. 15, 2005, vol. 74A, No. 4, pp. 722-738.

Xu, Ruijian et al., "Low permeability biomedical polyurethane nanocomposites", Journal of Miomedical Materials Resarch, 2003, vol. 64A, pp. 114-119.

Yang, M. et al., J. biomed. Mater. Res. 48 (1999) 13-23.

Yeh, J. et al., "Moisture diffusivity of Biomer® versus Biomer®-coated Polyisobutylene polyurethane urea (PIB-PUU): a potential blood sac material for the artificial heart", Journal of Materials Science Letters 13(19), 1994, pp. 1390-1391.

Yoon, Sung C. et al., "Surface and bulk structure of segmented poly(ether urethanes) with Perfluoro Chain Extenders. 5. Incorporation of Poly(dimethylsiloxane) and Polyisobutylene Macroglycols", Macromolecules Mar. 14, 1994, 27(6), pp. 1548-1554.

* cited by examiner

US 8,501,831 B2

POLYISOBUTYLENE URETHANE, UREA AND URETHANE/UREA COPOLYMERS AND MEDICAL DEVICES CONTAINING THE SAME

STATEMENT OF RELATED APPLICATION

This application is a continuation of U.S. application Ser. No. 12/492,483, filed Jun. 26, 2009, which is a non-provisional application of U.S. provisional application 61/076,327, filed Jun. 27, 2008, which are incorporated herein by reference in their entirety for all purposes.

FIELD OF THE INVENTION

The present invention relates to urethane, urea and urethane/urea copolymers and to medical devices containing the same.

BACKGROUND OF THE INVENTION

The use of polymeric materials in medical devices for implantation or insertion into the body of a patient is common in the practice of modern medicine. For example, polymeric materials such as silicone rubber, polyurethane, and fluoropolymers, for instance, polytetrafluoroethylene (PTFE), expanded PTFE (ePTFE) and ethylene tetrafluoroethylene (ETFE), are used as coating materials/insulation for medical leads, providing mechanical protection, electrical insulation, or both.

As another example, drug elating stents are known which have polymeric coatings over the stent to release a drug to counteract the effects of in-stent restenosis. Specific examples of drug eluting coronary stents include commercially available stents from Boston Scientific Corp. (TAXUS, PROMOS), Johnson & Johnson (CYPHER), and others. See S. V. Ranade et al., *Acta Biomater.* 2005 January; 1(1); 137-44 and R. Virmani et al. *Circulation* 2004 Feb. 17, 109(6) 701-5. Various types of polymeric materials have been used in such polymeric coatings including, for example, homopolymers such as poly(n-butyl methacrylate) and copolymers such as poly(ethylene-co-vinyl acetate), poly(vinylidene fluoride-co-hexafluoropropylene), and poly(isobutylene-co-styrene), for example, poly(styrene-b-isobutylene-b-styrene) triblock copolymers (SIBS), which are described, for instance, in U.S. Pat. No. 6,545,097 to Pinchuk et al. SIBS triblock copolymers have a soft, elastomeric low glass transition temperature (Tg) midblock and hard elevated Tg endblocks. Consequently, SIBS copolymers are thermoplastic elastomers, in other words, elastomeric (i.e., reversibly deformable) polymer that form physical crosslinks which can be reversed by melting the polymer (or, in the case of SIBS, by dissolving the polymer in a suitable solvent). SIBS is also highly biocompatible.

SUMMARY OF THE INVENTION

The present invention pertains to polyisobutylene urethane copolymers, to polyisobutylene urea copolymers, to polyisobutylene urethane/urea copolymers, to methods of making such copolymers and to medical devices that contain such polymers.

According to certain aspects of the invention, polyurethanes, polyureas and polyurethane/polyureas are provided, which comprise a polyisobutylene segment, an additional polymeric segment that is not a polyisobutylene segment, and a segment comprising a residue of a diisocyanate.

According to other aspects of the invention, polyurethanes, polyureas and polyurethane/polyureas are provided, which comprise a polyisobutylene segment and end groups that comprise alkyl-, alkenyl- or alkynyl-chain-containing end groups.

These and other aspects and embodiments as well as various advantages of the present invention will become readily apparent to those of ordinary skill in the art upon review of the Detailed Description and any Claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention.

As is well known, "polymers" are molecules containing multiple copies (e.g., from 5 to 10 to 25 to 50 to 100 to 250 to 500 to 1000 or more copies) of one or mom constitutional units, commonly referred to as monomers. As used herein, the term "monomers" may refer to free monomers and to those that have been incorporated into polymers, with the distinction being clear from the contest in which the term is used.

Polymers may take on a number of configurations, which may be selected, for example, from linear, cyclic and branched configurations, among others. Branched, configurations include star-shaped configurations (e.g., configurations in which three or more chains emanate from a single branch point), comb configurations (e.g., configurations having a main chain and a plurality of side chains, also referred to as "graft" configurations), dendritic configurations (e.g., arborescent and hyperbranched polymers), and so forth.

As used herein, "homopolymers" are polymers that contain multiple copies of a single constitutional unit (i.e., monomer). "Copolymers" are polymers that contain multiple copies of at least two dissimilar constitutional unit.

As used herein, a "polymeric segment" or "segment" is a portion of a polymer. Segments can be unbranched or branched. Segments can contain a single type of constitutional unit (also referred to herein as "homopolymeric segments") or multiple types of constitutional units (also referred to herein as "copolymeric segments") which may be present, for example, in a random, statistical, gradient, or periodic (e.g., alternating) distribution.

As used herein a soft segment is one that displays a Tg that is below body temperature, more typically from 35° C. to 20° C. to 0° C. to −25° C. to −50° C. or below. A hard segment is one that displays a Tg that is above body temperature, more typically from 40° C. to 50° C. to 75° C. to 100° C. or above. Tg can be measured by differential scanning calorimetry (DSC), dynamic mechanical analysis (DMA) and thermomechanical analysis (TMA).

Polyurethanes are a family of copolymers that are synthesized from polyfunctional isocyanates (e.g., diisocyanates, including both aliphatic and aromatic diisocyanates) and polyols (e.g., macro glycols). Commonly employed macroglycols include polyester diols, polyether diols and polycarbonate diols. Typically, aliphatic or aromatic diols or diamines are also employed as chain extenders, for example, to impart improved physical properties to the polyurethane. Where diamines are employed as chain extenders, urea linkages are formed and the resulting polymers may be referred to as polyurethane/polyureas.

Polyureas are family of copolymers that are synthesized from polyfunctional isocyanates and polyamines, for example, diamines such as polyester diamines, polyether diamines, polysiloxane diamines, polyhydrocarbon diamines and polycarbonate diamines. As with, polyurethanes, aliphatic or aromatic diols or diamines may be employed as chain extenders.

Urethane, urea and urethane/urea copolymers in accordance with the invention typically comprise one or more polyisobutylene segments. For example, according to certain aspects of the invention, polyisobutylene urethane, urea and urethane/urea copolymers are provided, which contain (a) one or more polyisobutylene segments, (b) one or more additional polymeric segments (other than polyisobutylene segments), and (c) one or mom segments that contains one or more diisocyanate residues and, optionally, one or more chain extender residues.

Examples of additional polymeric segments include soft polymeric segments such as polyether segments, fluoropolymer segments including fluorinated polyether segments, polyester segments, poly(acrylate) segments, poly(methacrylate) segments, polysiloxane segments and polycarbonate segments.

Examples of soft polyether segments include linear, branched and cyclic homopoly(alkylene oxide) and copoly (alkylene oxide) segments, including, homopolymeric and copolymeric segments formed from one or more of the following, among others: methylene oxide, dimethylene oxide (ethylene oxide), trimethylene oxide, propylene oxide, and tetramethylene oxide.

In this regard, in some embodiments, a polyether diol compatibilizer such as polytetramethylene oxide diol (PTMO diol) or polyhexametheylene oxide diol (PHMO diol) may be added to the polyisobutylene diol during the synthesis process in order to promote uniform distribution of the polyurethane hard segments into the PIB soft segments and to achieve favorable micro-phase separation in the polymer. Such polyalkylene oxides may also improve key mechanical properties such as one or more of the following: tensile strength, tensile modulus, flexural modulus, elongation, tear strength, flex fatigue, tensile creep, and abrasion performance, among others. The soft segment composition in the reaction mixture can be varied by varying the weight ratio of PIB diol to polyether diol from, for example, 99:1 to 95:5 to 90:10 to 75:25 to 50:50 to 25:75 to 10:90 to 5:95 to 1:99, more preferably, from 90:10 to 85:15 to 80:20 to 75:35 to 70:30.

Similarly, the weight ratio of soft segment to hard segment in the polyurethanes of the invention can be varied, for example, from 99:1 to 95:5 to 90:10 to 75:25 to 50:50 to 25:75 to 10:90 to 5:95 to 1:99, more preferably, 95:5 to 90:10 to 80:20 to 70:30 to 65:35 to 60:40 to 50:50, to achieve a variety of Shore hardness, a wide range of physical and mechanical properties, and an array of functional performance.

Examples of soft fluoropolymer segments include perfluoroacrylate segments and fluoridated, polyether segments, for example, linear, branched and cyclic homopoly(fluorinated alkylene oxide) and copoly(fluorinated alkylene oxide) segments, including homopolymeric and copolymeric segments formed from one or more of the following, among others: perfluoromethylene oxide, perfluorodimethylene oxide (perfluoroethylene oxide), perfluorotrimethylene oxide and perfluoropropylene oxide.

Examples of soft polyester segments include linear, branched and cyclic homopolymeric and copolymeric segments formed from one or more of the following, among others: alkyleneadipates including ethyleneadipate, propyleneadipate, tetramethyleneadipate, and hexamethyleneadipate.

Examples of soft poly(acrylate) segments include linear, branched and cyclic homopoly(acrylate) and copoly(acrylate) segments, including homopolymeric and copolymeric segments formed from one or more of the following, among others: alkyl acrylates such as methyl acrylate, ethyl, acrylate, propyl acrylate, isopropyl acrylate, butyl acrylate, sec-butyl, acrylate, isobutyl acrylate, 2-ethylhexyl acrylate and dodecyl acrylate Examples of soft poly(methacrylate) segments include linear, branched and cyclic homopoly(methacrylate) and copoly (methacrylate) segments, including homopolymeric and copolymeric segments formed from one or more of the following, among others: alkyl methacrylates such as hexyl methacrylate, 2-ethylhexyl methacrylate, octyl methacrylate, dodecyl methacrylate and octadecyl methacrylate.

Examples of soft polysiloxane segments include linear, branched and cyclic homopolysiloxane and copolysiloxane segments, including homopolymeric and copolymeric segments formed from one or more of the following, among others: dimethyl siloxane, diethyl siloxane, and methylethyl siloxane.

Examples of soft polycarbonate segments include those comprising one or more types of carbonate units,

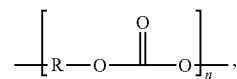

where R may be selected from linear, branched and cyclic alkyl groups. Specific examples include homopolymeric and copolymeric segments formed, from one or more of the following monomers, among others: ethylene carbonate, propylene carbonate, and hexamethylene carbonate.

Examples of additional polymeric segments also include hard polymeric segments such as poly(vinyl aromatic) segments, poly(alkyl acrylate) and poly(alkyl methacrylate) segments.

Examples of hard poly(vinyl aromatic) segments include linear, branched and cyclic homopoly(vinyl aromatic) and copoly(vinyl aromatic) segments, including homopolymeric and copolymeric segments formed from one or more of the following vinyl aromatic monomers, among others: styrene, 2-vinyl naphthalene, alpha-methyl, styrene, p-methoxystyrene, p-acetoxystyrene, 2-methylstyrenes, 3 methylstyrene and 4-methylstyrene.

Examples of hard poly(acrylate) segments include linear, branched and cyclic homopoly(alkyl acrylate) and copoly (alkyl acrylate) segments, including homopolymeric and copolymeric segments formed from one or more of the following acrylate monomers, among others: tert-butyl acrylate, hexyl, acrylate and isobornyl acrylate.

Examples of hard poly(alkyl methacrylate) segments include linear, branched and cyclic homopoly(alkyl methacrylate) and copoly(alkyl methacrylate) segments, including homopolymeric and copolymeric segments formed from one or more of the following alkyl methacrylate monomers, among others: methyl, methacrylate, ethyl methacrylate, isopropyl methacrylate, isobutyl methacrylate, t-butyl methacrylate, and cyclohexyl methacrylate.

The various polymeric segments described herein can vary widely in molecular weight, but typically are composed of between 2 and 100 repeat units (monomer units).

The various polymeric segments described herein can be incorporated into the polyurethanes, polyureas and polyurethane/polyureas of the invention by providing them in the form of polyols (e.g. diols, triols, etc.) and polyamines (e.g., diamines, triamines, etc.). Although the discussion to follow is generally based on the use of polyols. It is to be understood that analogous methods may be performed and analogous compositions may be created using polyamines and polyol/polyamine combinations.

Specific examples of polyisobutylene polyols include linear polyisobutylene diols and branched (three-arm) polyisobutylene triols. See, e.g., J. P. Kennedy et al., "Designed Polymers by Carbocationic Macromolecular Engineering: Theory and Practice," Hanser Publishers 1991, pp, 191-193, Joseph P. Kennedy, *Journal of Elastomers and Plastics* 1985 17: 82-88, and the references cited therein. More specific examples include linear polyisobutylene diols with a terminal —OH functional group at each end. Further examples of polyisobutylene polyols include poly(styrene-co-isobutylene)diols include poly(styrene-d-isobutylene-b-styrene)diols which may be formed, for example, using methods analogous to those described in the preceding Kennedy references. Examples of polyether polyols include polytetramethylene oxide diols, which are available from various sources including Sigma-Aldrich Co., Saint Louis, Mo., USA and E.I. duPont de Nemours and Co., Wilmington, Del., USA. Examples of polysiloxane polyols include polydimethylsiloxane diols, available from various sources including Dow Corning Corp., Midland Mich., USA, Chisso Corp., Tokyo, Japan. Examples of polycarbonate polyols include polyhexamethylene carbonate diols such as those available from Sigma-Aldrich Co. Examples of polyfluoroalkylene oxide diols include ZDOLTX, Ausimont, Bussi, Italy, a copolyperfluoroalkylene oxide diol containing a random distribution of —$CF_2CF_2O$— and —$CF_2O$— units, end-capped by ethoxylated unite, i.e., $H(OCH_2CH_2)_nOCH_2CF_2O(CF_2CF_2O)_p(CF_2O)_qCF_2CF_2O(CF_2CH_2O)_nH$, where n, p and q are integers. Polystyrene diol ($\alpha,\omega$-dihydroxy-terminated polystyrene) of varying molecular weight is available from Polymer Source, Inc., Montreal Canada. Polystyrene dials and three-arm triols may be formed, for example, using procedures analogous to those described in M. Weiβmüller et al., "Preparation, and end-linking of hydroxyl-terminated polystyrene star macromolecules," *Macromolecular Chemistry and Physics* 200(3), 1999, 541-551.

In some embodiments, polyols (e.g., diols, triols, etc.) are employed which are based on block copolymers. Examples of such block copolymer polyols include poly(tetramethylene oxide-b-isobutylene)diol, poly(tetramethylene oxide-b-isobutylene-b-alkylene oxide)diol, poly(dimethyl siloxane-b-isobutylene)diol, poly(dimethyl siloxane-b-isobutylene-b-dimethyl siloxane)diol, poly(hexamethylene carbonate-b-isobutylene)diol, poly(hexamethylene carbonate-b-isobutylene-b-hexamethylene carbonate)diol, poly(methyl methacrylate-b-isobutylene)diol, poly(methyl methacrylate-b-isobutylene-b-methyl methacrylate)diol, poly(styrene-b-isobutylene)diol and poly(styrene-b-isobutylene-b-styrene) diol (SIBS diol).

As noted above, polyisobutylene urethane, urea and urethane/urea copolymers in accordance with the invention typically contain one or more segments that contain one or more diisocyanate residues and, optionally, one or more chain extender residues.

Diisocyanates for use in forming the urethane, urea and urethane/urea copolymers of the invention include aromatic and non-aromatic (e.g., aliphatic) diisocyanates. Aromatic diisocyanates may be selected from suitable members of the following, among others: 4,4'-methylenediphenyl diisocyanate (MDI), 2,4- and/or 2,6-toluene diisocyanate (TDI), 1,5-naphthalene diisocyanate (NDI), para-phenylene diisocyanate, 3,3'-tolidene-4,4'-diisocyanate and 3,3'-dimethyl-diphenylmethane-4,4'-diisocyanate. Non-aromatic diisocyanates may be selected from suitable members of the following, among others: 1,6-hexamethylene diisocyanate (HDI), 4,4'-dicyclohexylmethane diisocyanate, 3-isocyanatomethyl-3,5,5-trimethylcyclohexyl isocyanate (Isophorone diisocyanate or IPDI), cyclohexyl diisocyanate, and 2,2,4-trimethyl-1,6-hexamethylene diisocyanate (TMDI).

Optional chain extenders are typically aliphatic or aromatic diols (in which case a urethane bond is formed upon reaction with an isocyanate group) or aliphatic or aromatic diamines (in which case a urea bond is formed upon reaction with an isocyanate group). Chain extenders may be selected from suitable members of the following, among others: alpha, omega-alkane diols such as ethylene glycol (1,2-ethane diol), 1,4-butanediol, 1,6-hexanediol, alpha,omega-alkane diamines, such as ethylene diamine, dibutylamine (1,4-butane diamine) and 1,6-hexanediamine, or 4,4'-methylene bis (2-chloroaniline).

Chain extenders may be also selected from suitable members of the following, among others: short chain diol polymers (e.g., alpha,omega-dihydroxy-terminated polymers having a molecular weight less than or equal to 1000) based on hard and soft polymeric segments (more typically soft polymeric segments) such as those described above, including short chain polyisobutylene diols, short chain polyether polyols such as polytetramethylene oxide diols, short chain polysiloxane diols such as polydimethylsiloxane diols, short chain polycarbonate diols such as polyhexamethylene carbonate diols, short chain poly(fluorinated ether)diols, short chain polyester diols, short chain polyacrylate diols, short chain polymethacrylate diols, and short chain poly(vinyl aromatic)diols. As is known in the polyurethane art, chain extenders can increase the hard-segment length (or, stated another way, can increase the ratio of hard segment material to soft segment material in the urethane, urea or urethane/urea polymer), which can in turn result in a polymer with higher modulus, lower elongation at break, and increased strength.

In certain other aspects of the invention, polyisobutylene urethane, urea and urethane/urea copolymers are provided, which comprise (a) one or more polyisobutylene segments, (b) optionally, one or more additional segments other than polyisobutylene segments, (c) one or more diisocyanate residues, (d) optionally, one or more chain extender residues, and (e) end groups that comprise alkyl, alkenyl or alkynyl chains ranging from 1 to 18 carbons in length. For example, such end groups may be selected from [—$CH_2]_n$—$CH_3$ groups, [—$CH_2]_n$—$CF_3$ groups, [—$CH_2]_n$—$C_6H_5$ groups (i.e., [—$CH_2]_n$-ph) and combinations thereof, among others, where n ranges from 1 to 17 (e.g., 1 to 2 to 3 to 4 to 5 to 6 to 7 to 8 to 9 to 10 to 11 to 12 to 13 to 14 to 15 to 16 to 17).

Polyisobutylene urethane, urea and urethane/urea copolymers in accordance with the invention may the synthesized, for example, in bulk or using a suitable solvent (e.g., one capable or dissolving the various species that participate in the polymerisation reaction). In certain, embodiments, polyisobutylene urethane, urea and urethane/urea copolymers in accordance, with tire invention are synthesized via reactive extrusion.

In certain embodiments, the biostability and/or biocompatibility of the polyisobutylene urethane, urea and urethane/urea copolymers in accordance with the invention can be improved by end-capping the copolymers with short aliphatic chains (e.g., [—$CH_2]_n$—$CH_3$ groups, [—$CH_2]_n$—$C(CH_3)_3$ groups, [—$CH_2]_n$—$CF_3$ groups, [—$CH_2]_n$—$C(CF_3)_3$ groups [—$CH_2]_n$—$CH_2OH$ groups, [—$CH_2]_n$—$C(OH)_3$ groups and [—$CH_2]_n$—$C_6H_5$ groups, etc., where n may range, for example, from 1 to 2 to 5 to 10 to 15 to 20, among others values) that can migrate to the polymer surface and self assemble irrespective of synthetic process to elicit desirable immunogenic response when, implanted in vivo. Alternatively, a block copolymer or block terpolymer with short aliphatic chains (e.g., [—$CH_2$]$_n$-b-[—$CH_2O$]$_n$—$CH_3$ groups, [—$CH_2$]$_n$-b-[—$CH_2O$]$_n$—$CH_2CH_2C(CH_3)_3$ groups, [—$CH_2$]$_n$-b-[—$CH_2O$]$_n$—$CH_2CH_2CF_3$ groups, [—$CH_2$]$_n$-b-[—$CH_2O$]$_n$—$CH_2CH_2C(CF_3)_3$ groups, [—$CH_2$]$_n$-b-[—$CH_2O$]$_n$—$CH_2CH_2OH$ groups, [—$CH_2$]$_n$-b-[—$CH_2O$]$_n$—$C(OH)_3$ groups, [—$CH_2$]$_n$-b-[—$CH_2O$]$_n$—$CH_2CH_2$—$C_6H_5$ groups, etc., where n may range, for example, from 1 to 2 to 5 to 10 to 15 to 20, among others values) that can migrate to the surface and self assemble can be blended with the copolymer toward the end of synthesis, in case of reactive extrusion it can be blended just before the extrudate emerges from the extruder.

Various synthetic strategies may be employed to create polyisobutylene urethane, urea and urethane/urea polymers in accordance with the invention. These strategies typically involved the reaction of (a) one or more polyol (commonly diol) species and one or more polyisocyanate (commonly diisocyanate) species, (b) one or more polyamine (commonly diamine) species and one or mom polyisocyanate species, or (c) one or more polyol species, one or mom polyamine species and one or more polyisocyanate species. Reaction may be conducted, for example, in inorganic solvents, or using supercritical $CO_2$ as a solvent. Ionomers can be used for polymer precipitation.

As previously indicated, although the discussion to follow is generally based on the use of polyols, it is to be understood that analogous methods may be performed and analogous compositions may be created using polyamines and polyol/polyamine combinations.

For example, in certain embodiments, a one step method may be employed in which a first macrodiol (M1) (e.g., a block copolymer diol such as SIBS diol, etc.) and a diisocyante (DI) (e.g., MDI, TDI, etc.) are reacted in a single step. Molar ratio of diisocyanate relative to the brat macrodiol, is 1:1. Using this technique a polyurethane having alternating macrodiol and diisocyante residues, i.e., -[DI-M1-]$_n$, where n is an integer, may be formed. In some embodiments, a diol or diamine chain extender (CE) (e.g., 1,2-ethane diol, 1,4-butanediol, 1,6-hexanediol, etc.) is included in the reaction mixture, in which case the molar ratio of diisocyanate relative to the combination of the first macrodiol and the chain extender is 1:1. For example, the ratio DI:M1:CE may equal 2:1:1, may equal 2:5:0.5, may equal 2:0.5:1.5, among many other possibilities. Where a ratio of DI:M1:CE equal to 2:1:1 is employed, a polyurethane having the following structure may be formed -[DI-M1-DI-CE-]$_n$. Reactions of this type have been reported to follow a statistical distribution, so M1 and CE residues are not likely to be perfectly alternating as shown. See, e.g., F. Wang, "Polydimethylsiloxane Modification of Segmented Thermoplastic Polyurethanes and Polyureas, Ph.D. dissertation, Virginia Polytechnic institute and State University, Apr. 13, 1998.

In other embodiments, a two-step reaction is employed wherein the first macrodiol and diisocyante are reacted in a single step at a DI:M1 molar ratio of ≧2:1 in order to form isocyanate-end-capped "prepolymers," DI-M1-DI. Then, in a second step, a chain extender is added, along with additional diisocyanate, if required to maintain an overall molar ratio of diisocyanate relative to the combination of the first macrodiol and the chain extender of 1:1. As above, where a molar ratio of DI:M1:CE equal to 2:1:1 is employed, a polyurethane having the following structure may be formed -[DI-M1-DI-CE-]$_n$, although the M1 and CE residues may not be perfectly alternating as shown. Due to enhanced reaction control, polyurethanes made by the two-step method tend to have a more regular structure than corresponding polyurethanes made by the one step method.

In certain other embodiments, a one step method may be employed in which a first macrodiol (M1) (e.g., a polyisobutylene diol, a SIBS diol, etc.), a second macrodiol (M2) (e.g., a polyether diol, a fluoropolymer diol, a polysiloxane diol, a polycarbonate diol, a polyester diol, a polyacrylate diol, a polymethacrylate diol, a polystyrene diol, etc.) and a diisocyante (DI) (e.g., MDI, TDI, etc.) are reacted in a single step. Molar ratio of diisocyanate relative to the first and second diols is 1:1. For example, the ratio DI:M1:M2 may equal 2:1:1, may equal 2:1.5:0.5, may equal 2:0.5:1.5, among many other possibilities. Where a ratio of DI:M1:M2 equal to 2:1:1 is employed, a polyurethane having the following structure may be formed -[DI-M1-DI-M2-]$_n$ although the chains are unlikely to be perfectly alternating as shown. In some embodiments, a chain extender is added to the reaction mixture, such that the molar ratio of diisocyanate relative to the first and second macrodiols and chain extender is 1:1. For example, the ratio DI:M1:M2:CE may equal 4:1:1:2, may equal 2:0.67:0.33:1, may equal 2:0.33:0.67:1, or may equal 5:1:1:3, among many other possibilities. Where a ratio of DI:M1:M2:CE equal to 4:1:1:2 is employed, a polyurethane having the following structure may be formed -[DI-M1-DI-CE-DI-M2-DI-CE-]$_n$, although the chains are unlikely to be perfectly alternating as shown.

In some embodiments, a two-step method is employed in which first and second macrodiols and diisocyante are reacted in a ratio of DI:M1:M2 of ≧2:1:1 in a first step to form isocyanate capped first and second macrodiols, for example DI-M1-DI and DI-M2-DI. In a second step, a chain extender is added which reacts with the isocyanate end caps of the macrodiols. In some embodiments, the number of moles of hydroxyl or amine groups of the chain extender may exceed the number of moles of isocyanate end caps for the macrodiols, in which case additional diisocyante may be added in the second step as needed to maintain a suitable overall stoichiometry. As above, the molar ratio of diisocyanate relative to the total of the first macrodiol, second macrodiol, and chain extender is typically 1:1, for example, DI:M1:M2:CE may equal 4:1:1:2, which may in theory yield an idealized polyurethane having the following repeat structure -[DI-M1-DI-CE-DI-M2-DI-CE-]$_n$, although the chains are unlikely to be perfectly alternating as shown. In other examples, the DI:M1:M2:CE ratio may equal 4:1.5:0.5:2 or may equal 5:1:1:3, among many other possibilities.

In some embodiments, three, four or more steps may be employed in which a first macrodiol and diisocyante are reacted in a first step to form isocyanate capped first macrodiol, typically in a DI:M1 ratio of ≧2:1 such that isocyanate end caps are formed at each end of the first macrodiol (although other ratios are possible including a DI:M1 ratio of 1:1, which would yield an average of one isocyanate end caps per macrodiol). This step is followed by second step in which the second macrodiol is added such that it reacts with one or both isocyanate end caps of the isocyanate capped first macrodiol. Depending on the relative ratios of DI, M1 and M2, this step may be used to create structures (among other statistical possibilities) such as M2-DI-M1-DI-M2 (for a DI:M1:M2 ratio of 2:1:2), M2-DI-M1-DI (for a DI:M1:M2 ratio of 2:1:1), or M1-DI-M2 (for a DI-M1:M2 ratio of 1:1:1).

In certain embodiments, a mixed macrodiol prepolymer, such as one of those in the prior paragraph, among others (e.g., M2-DI-M1-DI-M2, M1-DI-M1-DI-M1, DI-M1-DI-M2, etc.) is reacted simultaneously with a diol or diamine chain extender and a diisocyanate, as needed to maintain stoichiometry. For example, the chain extension process may be used to create idealized structures along the following lines, among others: -[DI:M2-DI-M1-DI-M2-DI-CE-]$_n$, -[DI-M1-DI-M2-DI-M1-DI-CE-]$_n$ or -[DI-M1-DI-M2-DI-CE-]$_n$, although it is again, noted that the chains are not likely to be perfectly alternating as shown.

In certain other embodiments, a mixed macrodiol prepolymer is reacted with sufficient diisocyanate to form isocyanate end caps for the mixed macrodiol prepolymer (e.g., yielding DI-M2-DI-M1-DI-M2-DI, DI-M1-DI-M2-DI-M1-DI or DI-M1-DI-M2-DI, among other possibilities). This isocyanate-end-capped mixed macrodiol can then be reacted with a diol or diamine chain extender (and a diisocyanate, as needed to maintain stochiometry). For example, the isocyanate-end-capped mixed macrodiol can be reacted with an equimolar amount of a chain extender to yield idealized structures of the following formulae, among others: -[DI-M2-DI-M1-DI-M2-DI-CE-]$_n$-[DI-M1-DI-M2-DI-M1-DI-CE-]$_n$ or -[DI-M1-DI-M2-DI-CE-]$_n$.

As noted above, in some embodiments of the invention, urethane, urea and urethane/urea, molecules having alkyl-, alkenyl- or alkynyl-chain-containing end groups such as [—CH$_2$]$_n$—CH$_3$ or [—CH$_2$]$_n$—CF$_3$ or [—CH$_2$]$_n$[—CH$_2$]$_n$—C$_6$H$_5$ end groups, among many others, are formed. For example, such polymers may be formed by reacting a urethane, urea or urethane/urea copolymer such as one of those described above with a molecule of the formula HO[—CH$_2$]$_n$—CH$_3$ or of the formula HO[—CH$_2$]$_n$—CF$_3$ or of the formula HO[—CH$_2$]$_n$—C$_6$H$_5$, preferably after ensuring that the urethane, urea or urethane/urea copolymer is provided with isocyanate end caps.

In accordance with various aspects of the invention, implantable and insertable medical devices are provided, which contain, one or more polymeric regions containing one or more polyisobutylene urethane, urea or urethane/urea copolymers. As used herein, a "polymeric region" is a region (e.g. an entire device, a device component, a device coating layer, etc) that contains polymers, for example, from 50 wt % or less to 75 wt % to 90 wt % to 95 wt % to 97.5 wt % to 99 wt % or more polymers.

Examples of medical devices for the practice of the present invention include implantable or insertable medical devices, for example, implantable electrical stimulation systems including neurostimulation systems such as spinal cord stimulation (SCS) systems deep brain stimulation (DBS) systems, peripheral, nerve stimulation (PNS) systems, gastric nerve stimulation systems, cochlear implant systems, and retinal implant systems, among others, and cardiac systems including implantable pacemaker systems, implantable cardioverter-defibrillators (ICD's), and cardiac resynchronization and defibrillation (CRDT) devices, including polymeric components for leads including lead insulation, outer body insulation, and components for the foregoing implantable electrical stimulation systems, stents (including coronary vascular stents, peripheral vascular stents, cerebral, urethral, ureteral, biliary, tracheal, gastrointestinal and esophageal stents), stent coverings, stent grafts, vascular grafts, valves including heart valves and vascular valves, abdominal aortic aneurysm (AAA) devices (e.g., AAA stents, AAA grafts, etc.), vascular access ports, dialysis ports, embolization, devices including cerebral aneurysm filler coils (including Guglilmi detachable cods and metal coils), embolic agents, tissue bulking devices, catheters (e.g., renal or vascular catheters such as balloon catheters and various central venous catheters), guide wires, baboons, fitters (e.g., vena cava filters and mesh, filters for distil protection devices), septal defect closure devices, myocardial plugs, patches, ventricular assist devices including left ventricular assist hearts and pumps, total artificial hearts, shunts, anastomosis clips and rings, and tissue engineering scaffolds for cartilage, bone, skin and other in vivo tissue regeneration, (e.g., porous scaffolds, electrospun films and membranes for tissue integration), urethral slings, hernia "meshes", artificial ligaments, orthopedic prosthesis, one grafts, spinal, disks, dental implants, biopsy devices, as well as any coated substrate (which can comprise, for example, metals, polymers, ceramics and combinations thereof) that is implanted or inserted into the body.

In some embodiments, the polymeric regions of the present invention correspond to an entire medical device. In other embodiments, the polymeric regions correspond to one or more portions of a medical device. For instance, the polymeric regions can be in the form of medical device components, in the form of one or more fibers which are incorporated into a medical device, in the form of one or more polymeric layers formed over all or only a portion of an underlying substrate, and so forth. Materials for use as underlying medical device substrates include ceramic, metallic and polymeric substrates. Layers can be provided over an underlying substrate at a variety of locations and in a variety of shapes (e.g., in the form of a series of rectangles, stripes, or any other continuous or non-continuous pattern). As used herein a "layer" of a given material is a region of that material whose thickness is small compared to both its length and width. As used herein a layer need not be planar, for example, taking on the contours of an underlying substrate. Layers can be discontinuous (e.g., patterned).

In certain preferred embodiments, polyisobutylene urethane, urea and urethane/urea copolymers in accordance with the present invention may be used to form inner or outer coatings for implantable electrical leads, may be used, to form lead body components (e.g., seal O-rings, etc.), or may be used to form polymeric components of pacemakers, defibrillators or heart failure devices, among many other applications.

Thus, polyisobutylene urethane, urea and urethane/urea copolymers in accordance with the present invention may be used to form lead insulation components through which at least one conductor extends, including single-lumen and multi-lumen extrusions and tubular (tube-shaped) insulation layers, as well as lead tip materials, headers, and various other lead components. Materials containing copolymers in accordance with the present invention may also be used as encapsulation/insulation materials for electronic signal generating/sensing components, examples of which include implantable pulse generators, implantable cardioverter-defibrillators (ICDs) and implantable cardiac resynchronization therapy (CRT) devices. Such electronic signal generating/sensing components may be used, for example, in conjunction with right ventricular lead systems, right atrial lead systems, and left atrial/ventricular lead systems and may be used to treat, for example, bradycardia, tachycardia (e.g., ventricular tachycardia) or cardiac dyssynchrony. In a vertebrate subject (including humans, pets and livestock). As previously noted, the present invention is also applicable to leads and electronic signal generating/sensing components for neurostimulation systems such as spinal cord stimulation (SCS) systems, deep brain stimulation (DBS) systems, peripheral nerve stimulation (PNS) systems, gastric nerve stimulation systems, cochlear implant systems, retinal implant systems, and pain management systems, among others.

Various known polyurethanes presently used in the medical device art (such as polyether, polyester, and polycarbonate based polyurethanes and/or their blends/copolymers with polydimethylsiloxane) can eventually exhibit environmental stress cracking upon insertion into a patient's body, due to the harsh (e.g., oxidative, hydrolytic, enzymatic, etc.) conditions that are encountered there. Where such polyurethanes are employed as lead insulation materials, such cracking can cause a breach in the insulation that allows bodily fluids to enter the lead and form shorts, for example, between the conductor(s) and/or the electronic components that generate current through the conductor(s). Moreover, slow corrosion of the metal conductor(s) within electrical leads is often encountered in the in vivo environment. The metal ions thus generated from the slow corrosion process are known to react with various insulation materials, including polyurethanes, causing metal ion oxidation (MIO) that can result in degradation and deterioration of the material. This can lead to rapid battery depletion and affect the ability of the device to reliably provide therapy.

The polyisobutylene urethane, urea and urethane/urea copolymers in accordance with, the present invention, on the other hand, are believed to possess enhanced biostability and biocompatibility. In this regard, it is believed that the polyisobutylene segments within the copolymer of the invention are highly resistant to degradation (e.g., oxidative, hydrolytic, enzymatic, metal ion, etc.) relative to known polyurethane soft segments such as polyether, polyester, and polycarbonate based polyurethanes and/or their blends/copolymers with polydimethylsiloxane. Polyisobutylene is also known to have good barrier properties and is biocompatible.

In addition to one or more polymers, the polymeric regions for use in the medical devices of the present invention may optionally contain, one or more supplemental agents.

For example, in some embodiments, an organically modified silicate is blended with the polymers forming the polymeric region as a supplemental agent. Such an agent may act to create a tortuous pathway for moisture thereby decreasing the moisture permeability of the region. Moreover, such silicates may maintain the strength and increase the modulus of the material. Supplemental agents further include agents such as alumina, silver nanoparticles, and silicate/alumina/silver nanoparticle composites.

In some embodiments, one or more therapeutic agents are included beneath, within (e.g., blended with), or attached to (e.g., covalently or non-covalently bound to) polymeric regions in accordance with the invention. "Therapeutic agents," "drugs," "pharmaceutically active agents," "pharmaceutically active materials," and other related terms may be used interchangeably herein.

A wide variety of therapeutic agents can be employed in conjunction with the present invention including those used for the treatment of a wide variety of diseases and conditions (i.e., the prevention of a disease or condition, the reduction or elimination of symptoms associated with a disease or condition, or the substantial or complete elimination of a disease or condition).

Exemplary therapeutic agents for use in conjunction with the present invention include the following: (a) anti-thrombotic agents such as heparin, heparin derivatives, urokinase, clopidogrel and PPack (dextrophenylalanine proline arginine chloromethylketone; (b) anti-inflammatory agents such as dexamethasone, prednisolone, corticosterone, budesonide, estrogen, sulfasalazine and mesalamine; (c) antineoplastic/ antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, transnational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (o) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function, of other client proteins/signal transduction, proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine) (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists, including PPAR-alpha, gamma and delta agonists, such as rosiglitazone, pioglitazone, netoglitazone, fenofibrate, bexaotone, metaglidasen, rivoglitazone and tesaglitazar, (bb) prostaglandin E agonists, including PGE2 agonists, such as alprostsdil or ONO 8815Ly, (cc) thrombin receptor activating peptide (TRAP), (dd) vasopeptidase inhibitors including benazepril, fosinopril, lisinopril, quinapril ramipril, imidapril, delapril, moexipril and spirapril, (ee) thymosin beta 4, (ff) phospholipids including phosphorylcholine, phosphatidylinositol and phosphatidylcholine, (gg) VLA-4 antagonists and VCAM-1 antagonists, (hh) non-fouling, protein resistant agents such as polyethyelene glycol and (it) prohealing agents.

Numerous therapeutic agents, not necessarily exclusive of those listed above, have been identified as candidates for vascular treatment regimens, for example, as agents targeting restenosis (antirestenotics). Such agents are useful for the practice of the present invention and include one or mom of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin, and bunazosine, β-antagonists such as propranolol and α/β-antagonists such as labetalol and carvedilol, (e) endothelin receptor antagonists such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as wed as C-nitroso-compounds, O-nitroso-compounds, N-nitroso-compounds and L-arginine, (g) Angiotensin Converting Enzyme (ACE) inhibitors sued as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin, inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid SOD (orgotein) and SOD mimics, verteporfin, rostaporfin, AGI 1067, and M40419, (w) agents affecting various growth factors including FGF pathway agents such as bFGF antibodies and chimeric fusion, proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof. Thromboxane A2 (TXA2) pathway modulators such as sulotroban, vapiprost dazoxiben and ridogrel, as web as protein tyrosine kinase inhibitors such as tyrphostin, genistein and quinoxaline derivatives, (x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518, (y) cell, motility inhibitors such as cytochalasin B, (z) anti-proliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen, mustards, alkyl sulfonates, ethylenimines, antibiotics (e.g., daunorubicin, doxorubicin), nitrosoureas, cisplatin agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), olimus family drugs (e.g., sirolimus, everolimus, tacrolimus, zotarolimus, etc.), cerivastatin, flavopiridol and suramin, (aa) matrix, deposition/organization pathway inhibitors such as halofuginone or other quinazolinone derivatives, pirfenidone and tranilast, (bb) endothelialization facilitators such as VEGF and RGD peptide, (cc) blood rheology modulators such as pentoxifylline and (dd) glucose cross-link breakers such as alagebrium chloride (ALT-711).

Where a therapeutic agent is present, a wide range of loadings may be used in conjunction with the medical devices of the present invention. Typical therapeutic agent loadings range, for example, from than 1 wt % or less to 2 wt % to 5 wt % to 10 wt % to 23 wt % or more of the polymeric region.

Numerous techniques are available for forming polymeric regions in accordance with the present invention.

For example, where the polyisobutylene urethane, urea or urethane/urea copolymers of the invention have thermoplastic characteristics, a variety of standard thermoplastic processing techniques may be used to form, polymeric regions from the same. Using these techniques, a polymeric region can be formed, for instance, by (a) first providing a melt that contains polymer(s) and any other optional agents such as silicates, therapeutic agents, and so forth, and (b) subsequently cooling the melt. Examples of thermoplastic processing techniques include compression molding, injection molding, blow molding, spraying, vacuum forming and calendaring, extrusion into sheets, fibers, rods, tubes and other cross-sectional profiles of various lengths, and combinations of those processes. Using these and other thermoplastic processing techniques, entire devices or portions thereof can be made.

Other processing techniques besides thermoplastic processing techniques may also be used to form the polymeric regions of the present invention, including solvent-based techniques. Using these techniques, polymeric regions can be formed, for instance, by (a) first providing a solution or dispersion that contains polymer(s) and any optional agents such as therapeutic agents, silicates and so forth, and (b) subsequently removing the solvent. The solvent that is ultimately selected will contain one or more solvent species, which are generally selected based on their ability to dissolve tire polymer(s) that form the polymeric region, in addition to other factors, including drying rate, surface tension, etc. In certain embodiments, die solvent is selected based on its ability to dissolve or disperse the optional agents, if any. Thus, optional agents such as therapeutic agents, silicates, and so forth may be dissolved or dispersed in the coating solution. Preferred solvent-based techniques include, but are not limited to, solvent casting techniques, spin coating techniques, web coating techniques, spraying techniques, dipping techniques, techniques involving coating via mechanical suspension including air suspension, ink jet techniques, electrostatic techniques, and combinations of these processes.

In some embodiments of the invention, a polymer containing solution (where solvent-based processing is employed) or a polymer containing melt (where thermoplastic processing is employed) is applied to a substrate to form a polymeric region. For example, the substrate can correspond to all or a portion of an implantable or insertable medical device to which a polymeric coating is applied, for example, by spraying, extrusion, and so forth. The substrate can also be, for example, a template, such as a mold, from which the polymeric region is removed after solidification. In other embodiments, for example, extrusion and co-extrusion techniques, one or more polymeric regions are formed without the aid of a substrate. In a specific example, an entire medical device is extruded. In another example, a polymeric coating layer is co-extruded along with and underlying medical device body. In another example, a polymeric tube is extruded which is then assembled over a medical device substrate (e.g., on an electrical lead, either as an electrically insulating or electrically non-insulating jacket).

EXAMPLES

Example 1

One Step Synthesis Using Polyisobutylene Diol with Double Bonds

The following preparation of polyisobutylene polyurethane (PIBPU) is an example of a general procedure for the one-step bulk polymerization, of a polyisobutylene diol with double bonds (Allyl PIBDiol). The Allyl PIBDiol can be, for example, the following,

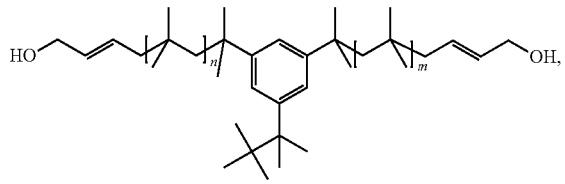

described in WO 2008/060333 A1 to Faust et al. where n and m may range, for example, from 2-100, more preferably 5-50, even more preferably 10-30.

To a 50 ml capacity two neck round bottomed flask equipped with a stirrer and condenser, add pre-dried allyl-polyisobutylene diol (Allyl PIBDiol) ($M_n$=2038 daltons, 10.0 g, 4.9 mM) (where m=15, n=15), and 1,4-butanediol (BDO) (0.44 g, 4.9 mM) and degas the mix lure at 70° C. for 3 h under vacuum (2 torr). Cool the contents of the flask to 60° C. and add tin(II) 2-ethylhexanoate [$Sn(Oct)_2$] (0.39 g, 0.98 mM) to the reaction contents under an inert atmosphere, float the reaction mixture to 85° C., and under vigorous stirring gradually add purified methylenebisphehylene diisocyanate (MDI) (2.45 g, 9.5 mM). Maintain, the reaction mixture at 85° C. under inert atmosphere and continue stirring for 5 h. Withdraw small aliquots from the reaction mixture at the end of 5 h and titrate for unreacted MDI to monitor the progress of polymerization. Continue the reaction to sufficient conversion. Cool the reaction contents to 45° C. and transfer the content's to a non-stick mold and allow the reaction to proceed to completion, holding at room temperature for 24-48 h.

Analogous procedures can be employed to prepare PIBPU with different Shore A hardness by varying the molar MDI:BDO:Allyl PIBDiol ratio, for example, from 3:2:1, 4:3:1, 4:2:2, 5:2:3, 5:3:2 and/or by varying the number average molecular weight of the Allyl PIBDiol, for example, from 1478 daltons (when n=10, m=10) to 3108 daltons (when n=25, m=25), however, m and n could be equal to, for example, m=2-100 and n=2-100, more preferably m=10-40 and n=10-40, among other values.

Example 2

One Step Synthesis Using Polyisobutylene Diol without Double Bonds

The following preparation of polyisobutylene poly urethane (PIBPU) without double bonds in the polyisobutylene diol (PIBdiol) is an example of a general procedure for the one-step bulk polymerization. The use of PIBdiol without unsaturation is preferred where it is desirable to minimise degradation caused, for example, by ultraviolet, thermal, oxidative, corrosive, enzymatic, and immunogenic factors. The PIBDiol can be, for instance, the following,

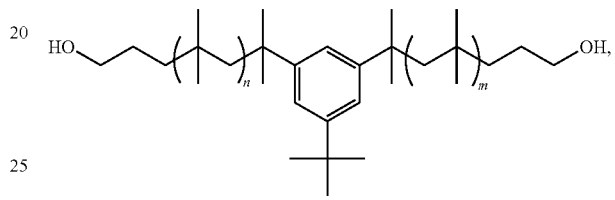

which is described in WO 2008/066914 A1 to Kennedy et al, where n and m range, for example, from 2-100, more preferably 5-50, even more preferably 10-30.

To a 50 ml capacity two neck round bottomed flask equipped with stirrer and condenser add pre-dried saturated polyisobutylene diol (PIBDiol) ($M_n$=2014 daltons, 10.0 g, 4.96 mM) (where m=15, n=15), and 1,4-butanediol (0.447 g, 4.96 mM) and degas the mixture at 7° C. for 3 h under vacuum (2 torr). Cool the contents of the flask to 60° C. and add $Sn(Oct)_2$ (0.39 g, 0.98 mM) to the reaction contents under inert atmosphere. Heat the reaction mixture, to 85° C., and under vigorous stirring gradually add purified methylenebisphehylene diisocyanate (MDI) (2.48 g, 9.93 mM). Maintain the reaction mixture at 85° C. under inert atmosphere and continue stirring for 5 h. Withdraw small aliquots from the reaction mixture at the end of 5 h and titrate for uureacted MDI to monitor the progress of polymerization. Continue the reaction to sufficient conversion. Cool the reaction contents to 45° C. and transfer the contents to a non-stick mold and allow the reaction to proceed to completion holding at mom temperature for 24-48 h.

Analogous procedures can be employed to prepare PIBPU with different Shore A hardness by varying the molar MDI:BDO:PIBDiol ratio, for example, from 3:2:1, 4:3:1, 4:2:2, 5:2:3, 5:3:2 and/or by varying the number average molecular weight of PIBDiol, for example, from 1454 daltons (when n=10, m=40) to 3134 daltons (when n=25, m=25), however, m and n could be equal to, for example, m=2-100 and n=2-100, more preferably m=10-40 and n=10-40, among other values.

Example 3

Two Step Synthesis Using Polyisobutylene Diol with Double Bonds

In a first step, allyl-polyisobutylene diol (Allyl PIBDiol) like that of Example 1 is mixed with a stoichiometric excess of MDI to form a pre-polymer. In a second step, 1,4-butanediol is added as a chain-extender to obtain the high molecular weight polyurethane. A representative procedure is described below.

To a 50 ml capacity two neck round bottomed flask equipped with a stirrer and condenser add pre-dried allyl-polyisobutylene diol ($M_n$=2038 daltons, 10.0 g, 4.9 mM), and degas the mixture at 70° C. for 3 h under vacuum (2 torr). Add $Sn(Oct)_2$ (0.39 g, 0.9 mM) under inert atmosphere and heat the reaction mixture to 85° C. and under vigorous stirring gradually add purified methylenebisphehylene diisocyanate (MDI) (2.45 g, 9.81 mM. Maintain, the reaction mixture at 85° C. under inert atmosphere and continue stirring for 1 h followed by addition of 1,4-butanediol (0.44 g, 4.9 mM). Withdraw small aliquots from the reaction mixture at the end of 5 h and titrate for unreacted MDI to monitor the progress of polymerization. Continue the reaction to sufficient conversion. Cool, the reaction, contents to 45° C. and transfer the contents to a non-stick mold and allow the reaction to proceed to completion holding at room temperature for 24-48 h.

Analogous procedures can be employed to prepare PIBPU with and/or without double bonds with different Shore A hardness, for example, by varying the molar MDI:BDO:PIB-Diol ratio from 3:2:1, 4:3:1, 4:2:2, 5:2:3, 5:3:2 and/or by varying the number average molecular weight of the Allyl PIBDiol, for example, torn 1478 to 3168 daltons (although m and n could be equal to, for example, m=2-100 and n=2-100, more preferably m×10-40 and n=10-40, among other values). In other processes, a polyisobutylene diol (PIBdiol) without double bonds, for example, having an average molecular weight of 1454 to 3134 daltons (although m and n could be equal to, for example, m=2-100 and n=2-100, more preferably m=10-40 and n=10-40, among other values) is used in place of the Allyl PIBDiol.

Example 4

Synthesis from Polyisobutylene Diol and Polyhexametheylene Oxide Diol

PIBPU having mixtures of PIB diol and polyether diol in different proportions as soft segments can be synthesized in a two-step process. The polyurethane hard segments are formed by BDO and MDI. The distribution of the polyol in the soft segment in this example is PIBDiol (75 wt %) and polyhexametheylene oxide diol (PHMO diol) (25 wt %).

PIB-PHMOPU can be synthesized as follows. Distill saturated PIBDiol ($M_n$=2014 daltons, 10 g, 4.96 mM) and polyhexametheylene oxide diol (PHMO diol) ($M_n$=1180, 3.22 g, 2.73 mmol) azeotropically from dry toluene (40 ml). Maintain this mixture at 60° C. for 2 hours under vacuum. In a separate round bottomed flask mix $Sn(Oct)_2$ (0.6 g, 0.149 Mmol) in 30 ml of dry toluene, add to die reaction mixture with stirring, and increase the temperature of the reaction mixture to 85° C. under dry inert gas. Add MDI (3.72 g, 14.88 mM) to this mixture under dry inert gas while vigorously stirring for 1 h. Add BDO (0.80 g, 9.02 mM) to the resulting reaction mixture under inert atmosphere and continue stirring for 5 hours at 110° C. Withdraw small aliquots from the reaction mixture at the end of 5 h and titrate for unreacted MDI to monitor the progress of polymerization. Continue the reaction to sufficient conversion. Cool the reaction contents to 45° C. and transfer the contents to a non-stick mold and allow the reaction to proceed to completion holding at mom temperature for 24-48 h. Dry the polymer under vacuum to constant weight.

Example 5

Synthesis from Polyisobutylene Diol and Polytetramethylene Oxide Diol

PIBPU having mixtures of FIB diol and polyether diol in different proportions as soft segments can be synthesized in a two-step process as follows. The polyurethane bard segments are formed by BDO and MDI. The distribution of the polyol in the soft segment in this example is PIBDiol (80 wt %) and polytetramethylene oxide diol (PTMO diol) (20 wt %).

PIB-PTMOPU can be synthesized as follows. Distill saturated PIBDiol ($M_n$=2014 daltons, 10 g, 4.96 mM) and polytetramethylene oxide diol (PTMO diol) ($M_n$=1080, 2.5 g, 2.31 mM) azeotropically from dry toluene (40 mL). Maintain this mixture at 60° C. for 2 hours under vacuum. In a separate round bottomed flask mix $Sn(Oct)_2$ (0.6 g, 0.149 Mmol) in 30 ml of dry toluene, add to the reaction mixture with stirring, and increase the temperature of the reaction mixture to 85° C. under dry inert gas. Add MDI (3.72 g, 14.88 mM) to this mixture under dry inert gas white vigorously stirring for 1 h. Add BDO (0.89 g, 9.92 mM) to the resulting reaction mixture under inert atmosphere and continue stirring for 5 hours at 110° C. Withdraw small aliquots from the reaction mixture at the end of 5 h and titrate for unreacted MDI to monitor the progress of polymerization. Continue the reaction to sufficient conversion. Cool the reaction contents to 45° C. and transfer the contents to a non-stick mold, and allow the reaction to proceed to completion: holding at room temperature for 24-48 h. Dry the polymer under vacuum to constant weight.

Example 6

Synthesis from Polyisobutylene Diol and Polytetramethylene Oxide Diol

PIBPU having mixtures of PIB diol and polyether diol in different proportions as soft segments can be synthesized in a two-step process as follows. The polyurethane hard segments are formed by BDO and MDI. The distribution of the polyol in the soft segment in this example is PIBDiol (90 wt %) and PTMO diol (10 wt %).

PIB-PTMOPU can be synthesized as follows. Distill saturated PIBDiol ($M_n$=2014 daltons, 10 g, 4.96 mM) and Polytetrametheylene oxide diol (PTMO diol) ($M_n$=1080, 1.11 g, 1.02 mM) azeotropically from dry toluene (40 mL). Maintain this mixture at 60° C. for 2 hours under vacuum. In a separate round bottomed flask mix $Sn(Oct)_2$ (0.4 g, 0.99 Mmol) in 30 ml of dry toluene, add to the reaction mixture with stirring, and increase the temperature of the reaction mixture to 85° C. under dry inert gas. Add MDI (2.48 g, 9.92 mM) to this mixture under dry inert gas while vigorously stirring for 1 h. Add BDO (0.44 g, 9.92 mM) to the resulting reaction mixture under inert atmosphere and continue stirring for 5 hours at 110° C. Withdraw small aliquots from the reaction, mixture at the end of 5 h and titrate for unreacted MDI to monitor the progress of polymerization. Continue the reaction to sufficient conversion. Cool the reaction contents to 45° C. and transfer the contents to a non-stick mold and allow the reaction to proceed, to completion holding at room temperature for 24-48 h. Dry the polymer under vacuum to constant weight.

Example 1

Reactive Extrusion

In certain embodiments, polyisobutylene urethane copolymers in accordance with the invention are synthesized via reactive extrusion. For example, a mixture of polyisobutylene diol (PIBdiol) and one or more optional additional diols, for instance 1,4-butanediol (BDO) and/or polyether diol (e.g., polytetramethylene oxide diol (PTMO diol) and/or polyhexamethylene oxide diol (PHMO diol), and a suitable catalyst (e.g., Sn(Oct)$_2$) can be fed into a twin screw compounding extruder using a suitable flow controller. Extruders of this type are described, for example, in U.S. Pat. No. 3,642,964 to Rausch Jr. et al. and U.S. Pat. No. 6,627,724 to Meijs et al. Methylenebisphehylene diisocyanate (MDI) can be fed into the extruder from a separate scarce using a separate flow controller. The extruder is operated at a temperature which promotes the polymerization process. The relative feed rates of PIBdiol, BDO, optional polyether diol (e.g., PTMO diol and/or PHMO diol), Sn(Oct)$_2$ and MDI can be varied to prepare polyurethane with variety of Shore hardness, a wide range of physical and mechanical properties, and an array of functional performance. The synthesis can be carried out as a one step process or in multiple steps.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A method for making an implantable or insertable medical device including a polyisobutylene urethane, urea or urethane/urea copolymer, the method comprising:
   reacting a diisocyanate, a polyisobutylene polyol or polyamine and a polyether diol to form a polyisobutylene urethane, urea or urethane/urea copolymer; and
   forming at least a portion of an implantable or insertable medical device from the polyisobutylene urethane, urea or urethane/urea copolymer,
   wherein the molar amount of the polyisobutylene reacted with the polyether diol is greater than or equal to the molar amount of polyether diol.

2. The method of claim 1, wherein the molar ratio of the polyisobutylene to the polyether diol is 1.5:0.5 to 1:1.

3. The method of claim 1, wherein the reacting step comprises:
   reacting the diisocyanate with the polyisobutylene polyol or polyamine and the polyether diol to form an isocyante-end-capped prepolymer; and
   reacting the isocyante-end-capped prepolymer with a chain extender.

4. The method of claim 3, wherein the chain extender includes at least one member selected from the group consisting of aliphatic diols, aromatic diols, aliphatic diamines, aromatic diamines.

5. The method of claim 3 wherein the molar ratio of the diisocyanate to polyisobutylene to chain extender is 2:1.5:0.5 to 2:0.5:1.5.

6. The method of claim 1, wherein the polyether diol includes at least one member selected from the group consisting of: methylene oxide, dimethylene oxide (ethylene oxide), trimethylene oxide, propylene oxide, and tetramethylene oxide.

7. The method of claim 1, wherein the diisocyanate includes at least one member selected from the group consisting of an aromatic diisocyanate, an aliphatic diisocyanate and combinations thereof.

8. The method of claim 1, wherein the diisocyanate is selected from the group consisting of 4,4'-methylenediphenyl diisocyanate, toluene diisocyanate, 1,5-naphthalene diisocyanate, para-phenylene diisocyanate, 3,3'-tolidene-4,4'-diisocyanate, 3,3'-dimethyl-diphenylmethane-4,4'-diisocyanate, and combinations thereof.

9. An implantable or insertable medical device comprising:
   a polyisobutylene urethane, urea or urethane/urea copolymer comprising:
   a residue of a diisocyanate;
   a residue of a polyisobutylene polyol or polyamine; and
   a residue of a polyether diol, wherein a molar amount of the polyisobutylene is greater than the molar amount of polyether diol.

10. The implantable or insertable medical device of claim 9, wherein the molar ratio of the polyisobutylene to the polyether diol is 1.5:0.5 to 1:1.

11. The implantable or insertable medical device of claim 9, and further comprising a residue of a chain extender.

12. The implantable or insertable medical device of claim 11, wherein the chain extender includes at least one member selected from the group consisting of aliphatic diols, aromatic diols, aliphatic diamines, aromatic diamines.

13. The implantable or insertable medical device of claim 11, the molar ratio of the diisocyanate to polyisobutylene to chain extender is 2:1.5:0.5 to 2:0.5:1.5.

14. The implantable or insertable medical device of claim 9, wherein the polyether diol includes at least one member selected from the group consisting of: methylene oxide, dimethylene oxide (ethylene oxide), trimethylene oxide, propylene oxide, and tetramethylene oxide.

15. The implantable or insertable medical device of claim 9, wherein the diisocyanate includes at least one member selected from the group consisting of an aromatic diisocyanate, an aliphatic diisocyanate and combinations thereof.

16. The implantable or insertable medical device of claim 9, wherein the diisocyanate includes at least one member selected from the group consisting of 4,4'-methylenediphenyl diisocyanate, toluene diisocyanate, 1,5-naphthalene diisocyanate, para-phenylene diisocyanate, 3,3'-tolidene-4,4'-diisocyanate, 3,3'-dimethyl-diphenylmethane-4,4'-diisocyanate, and combinations thereof.

17. The implantable or insertable medical device of claim 9, and further comprising at least one end group that comprise alkyl, alkenyl or alkynyl chains ranging from 1 to 17 carbons atoms in length.

* * * * *